United States Patent
Pagedas

[19]

[11] Patent Number: 5,368,597
[45] Date of Patent: Nov. 29, 1994

[54] RECLOSABLE POUCH FOR LAPAROSCOPIC USE

[76] Inventor: Anthony Pagedas, 8401 W. Edgerton, Greendale, Wis. 53129

[21] Appl. No.: 66,366

[22] Filed: May 24, 1993

[51] Int. Cl.$^5$ ............................................. A61B 17/00
[52] U.S. Cl. ................................. 606/114; 606/127; 606/110; 600/37
[58] Field of Search .............. 600/37; 128/749; 606/1, 606/113, 114, 110, 127, 151

[56] References Cited

U.S. PATENT DOCUMENTS

| | | | |
|---|---|---|---|
| 30,471 | 10/1860 | Dudley . | |
| 974,879 | 11/1910 | Gwinn . | |
| 1,609,014 | 11/1926 | Dowd . | |
| 3,908,661 | 9/1975 | Kramer . | |
| 4,557,255 | 12/1985 | Goodman | 606/127 |
| 4,611,594 | 9/1986 | Grayhack et al. . | |
| 4,997,435 | 3/1991 | Demeter | 606/127 |
| 5,074,867 | 12/1991 | Wilk | 606/128 |
| 5,147,371 | 9/1992 | Washington et al. | 606/127 |
| 5,163,942 | 11/1992 | Rydell | 606/113 |
| 5,176,687 | 1/1993 | Hasson et al. | 606/114 |
| 5,190,542 | 3/1993 | Nakao et al. | 606/114 |
| 5,190,555 | 3/1993 | Wetter et al. | 606/127 |
| 5,192,284 | 3/1993 | Pleatman | 606/127 |
| 5,192,286 | 3/1993 | Phan et al. | 606/127 |
| 5,215,521 | 6/1993 | Cochran et al. | 600/37 |
| 5,234,439 | 8/1993 | Wilk et al. | 606/127 |

FOREIGN PATENT DOCUMENTS

| | | | |
|---|---|---|---|
| 0025796 | 1/1984 | Brazil | 606/127 |
| 0499243 | 8/1992 | European Pat. Off. | 606/114 |

*Primary Examiner*—Stephen C. Pellegrino
*Assistant Examiner*—Glenn K. Dawson
*Attorney, Agent, or Firm*—Steven R. Ormiston

[57] ABSTRACT

Various embodiments of a reclosable pouch device and methods for using the device in surgery are shown and described. The reclosable pouch has a wand and a rod attached to the wand near the front and extending back generally parallel to the wand. A part of the rod is flexible for bowing out from the wand when the rod handle is pushed forward and for straightening to come close to the wand when the rod handle is pulled backward. The handle is a part of the rod near the back, which may be rigid, rigid and slidably connected to the wand, or flexible and slidably connected to the wand. A bag may be attached to the rod and wand for receiving a mass during surgery. When the rod bows out, the bag is opened. When the rod straightens, the bag is closed to form a seal. A preferred embodiment includes a slot system having a channel with the rod received in the channel, held in the channel for part of its length, and capable of bowing out of the channel for part of its length. Methods of using the device include insertion of the device through a laparoscopic sleeve for enclosure, manipulation, and retrieval of a mass.

13 Claims, 5 Drawing Sheets

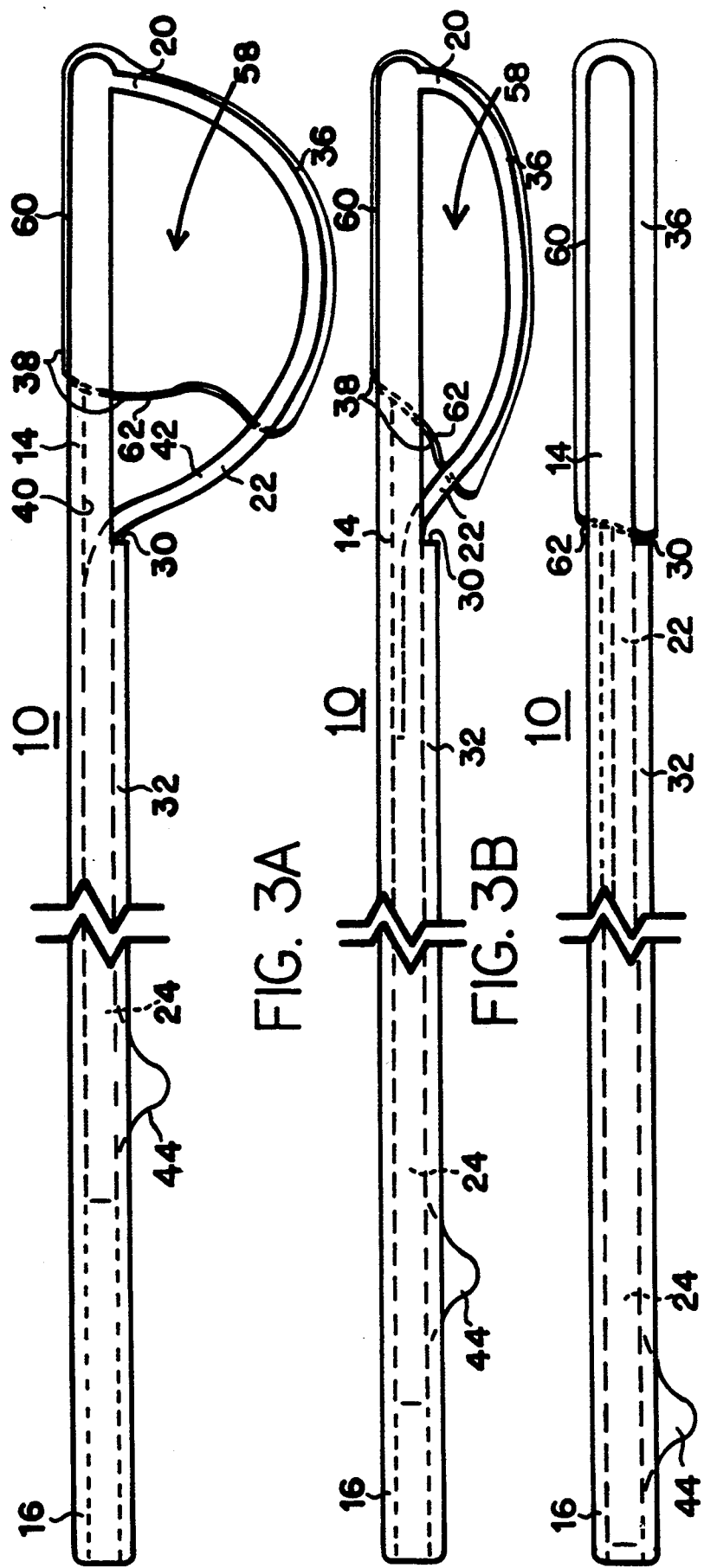

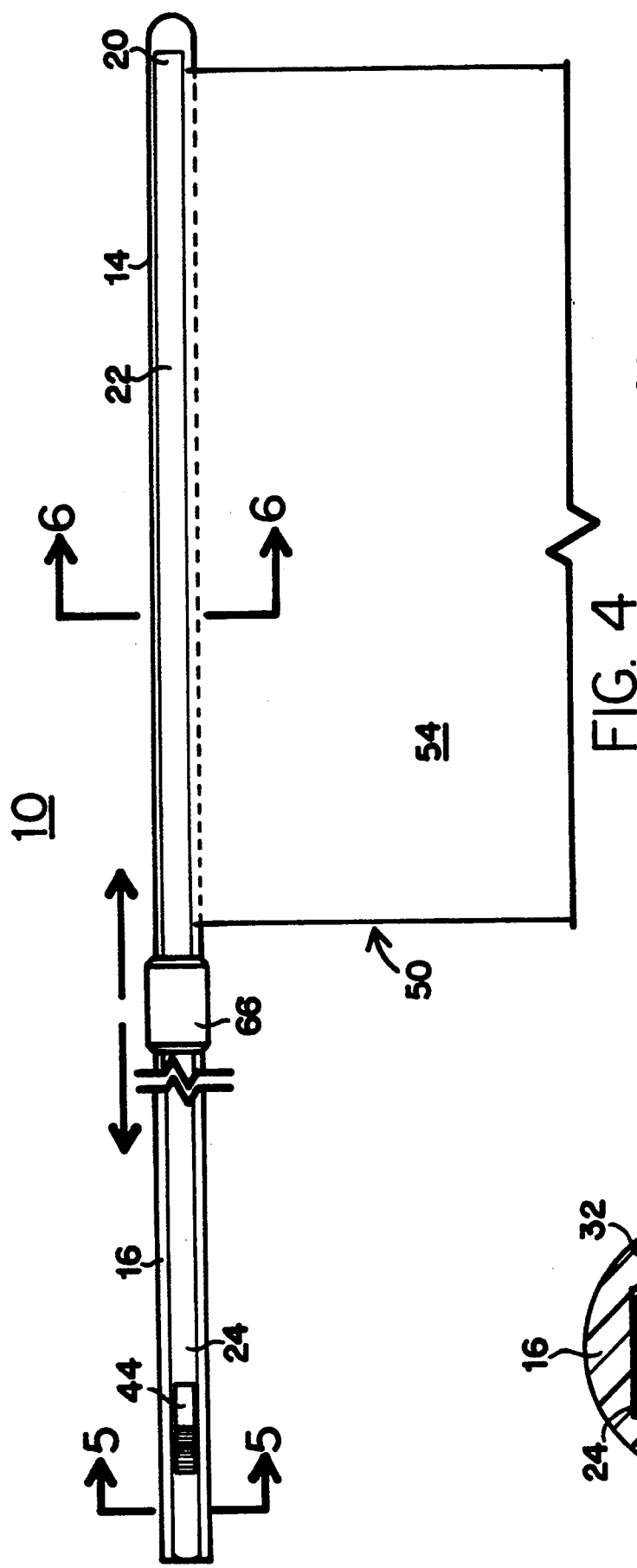
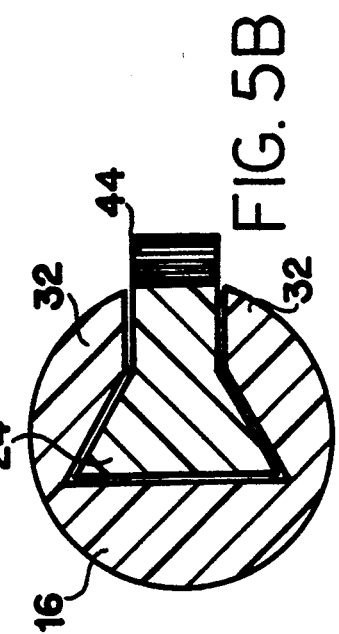
FIG. 5B
FIG. 4
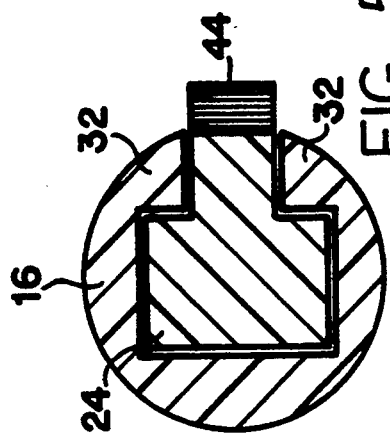
FIG. 5A

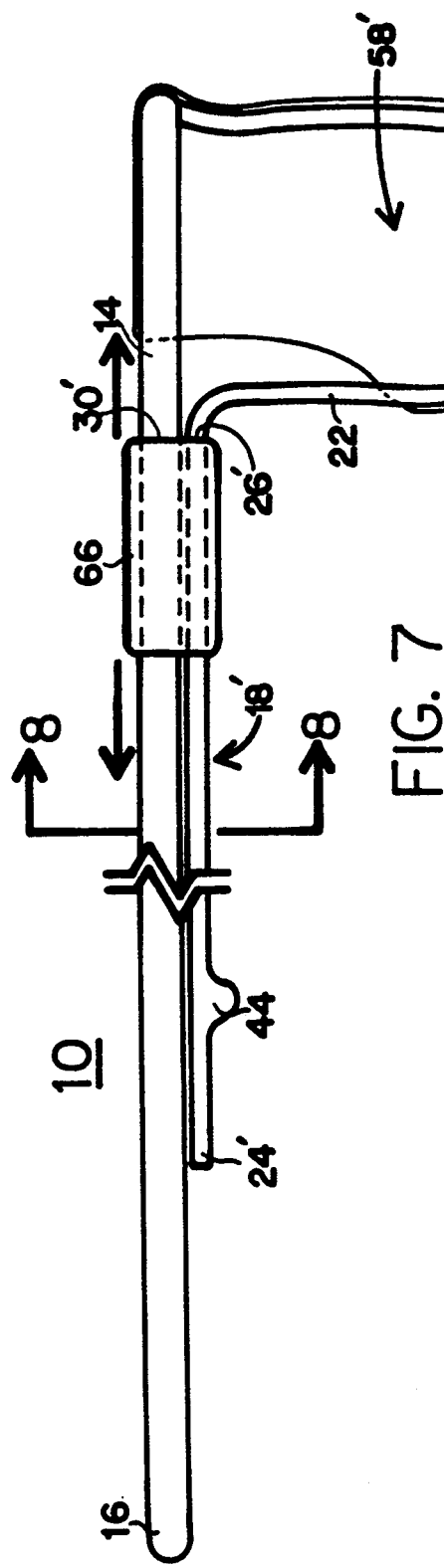
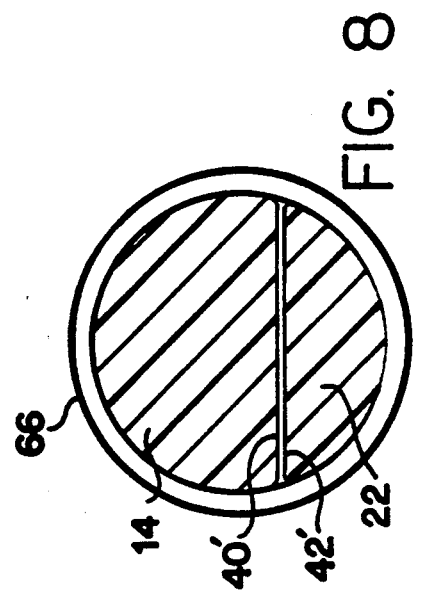
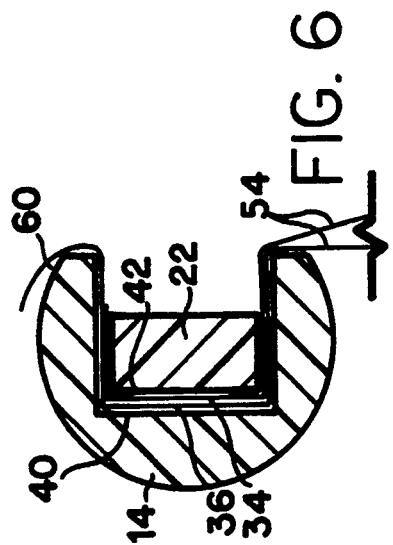

RECLOSABLE POUCH FOR LAPAROSCOPIC USE

FIELD OF THE INVENTION

This invention relates generally to internal surgery and, more specifically, to a surgical device and methods for accessing and retrieving tissue or other mass from a body cavity.

BACKGROUND OF THE INVENTION

In recent years, the applications for laparoscopic surgery have expanded to include many different procedures. A benefit of laparoscopic operations is the relatively quick recovery period experienced by patients, due to the small incisions that are made in the body. These incisions reduce the trauma and the required healing compared to traditional surgery. Laparoscopic tubes and sleeves with diameters on the order of 10 millimeters are inserted through the incisions to aid in accessing the tissue in the body cavity. Various instruments and a video camera are typically directed through the laparoscopic sleeves for performing and monitoring the surgical steps.

A particular concern in laparoscopic surgery is the transporting of tissues and other mass that are cut away or retrieved during the surgery. While moving, manipulating, or cutting up the mass within the body cavity, pieces of infected or cancerous mass, blood, bile, and other liquids may escape into the body cavity and pose infection problems or other complications. It is desirable to contain these materials in a bag or similar enclosure within the body cavity before removal to minimize the risk of infection or other complications. It is important that the containment of the materials be accomplished as quickly as possible with minimal disturbance to the surgical site.

Instruments with membranes or bags have been designed in an attempt to avoid the complications associated with the removal of tissue during laparoscopic surgery. One device is the pouch disclosed in Hasson, et al. (U.S. Pat. No. 5,176,687), which has a membrane circumferentially and concentrically attached to a conduit and has a concentric, distal entryway into the membrane. This membrane is closed with a drawstring with the help of a rigid extension separate from the membrane that extends forward of the conduit. Washington, deceased, et al. (U.S. Pat. No. 5,147,371) discloses a device with a wire forming a double loop and holding a bag at the end of a tube. The wire ends are pushed and pulled to expand and contract the radius of the loop to affect the size of the bag opening. In Wilk (U.S. Pat. No. 5,074,867), a pusher rod is used to push into the body cavity a membrane having attached strings that extend out of the laparoscopic sleeve. A forceps inserted through another laparoscopic sleeve is used to manipulate the membrane and place it around a piece of tissue. The strings are then pulled to remove the membrane from the body cavity. Demeter (U.S. Pat. No. 4,997,435) discloses a device with a first catheter having several struts extending forward and a second, inner catheter attached to a sheath that has a distal opening attached to the struts. By twisting the second catheter relative to the first, the sheath twists inside the struts to close the distal end of the sheath.

These devices tend to be cumbersome and time consuming to use. They cannot be operated with one hand and they typically require a second surgical instrument inserted through another laparoscopic sleeve to open and/or close the bag or membrane. Further, these devices do not provide for an adjustable opening that may be securely sealed upon containment of the object materials.

SUMMARY OF THE INVENTION

Accordingly, the general purpose and principal object of the invention is to provide a means for achieving greater efficiency, control and safety in containing materials within, and removing materials from, the body cavity during laparoscopic surgery.

Another object is to provide a device for removing material from a body cavity during laparoscopic surgery wherein the device may be accurately manipulated and controlled with one hand.

Another object is to provide a device for removing materials from a body cavity during laparoscopic surgery wherein the device has an adjustable opening that seals when closed.

Another object of the invention is to provide a device and method of operating same that allows materials to be removed from a body cavity during laparoscopic surgery in less time than is required using presently available devices and methods.

According to the present invention, the above and other objects are achieved by a novel surgical device for safely manipulating and retrieving tissue from a body cavity in operations such as laparoscopic surgery, and also a method for using the surgical device. The invented surgical device comprises an elongated wand and an elongated rod, which are attached near the front and are close to each other near the back so that they may be manipulated from outside a body cavity. A flexible portion of the rod may move to bow out from the wand near the front or may move to straighten and lie close to the wand. A bag may be attached to the wand and the rod for enclosing and retrieving material during surgery. The bag may be opened by pushing the rod forward relative to the wand to bow out the flexible portion and may be closed by pulling the rod backward relative to the wand to straighten the flexible portion.

The rod may be flexible in a portion of its length or along substantially the entire length. Embodiments with a rod having a flexible portion near the front and a rigid handle near the back may be held in the surgeon's hand or inserted through a laparoscopic sleeve so that the handle is close to the wand for being manipulated. In these embodiments, the change from rigid handle to flexible portion controls the location of the transition from the rod being close to the wand to bowing out from the wand. Alternatively, such embodiments may also include a connector that holds the handle of the rod close to the wand so that the rod slides relative to the wand. The connector may also extend to engage the flexible portion so that the portion of the connector controls the transition point rather than the location of change from rigid to flexible.

Embodiments with a rod that is flexible substantially along the length of the rod include a connector for holding the handle of the rod near the wand to guide the handle when it is pushed. The connector also extends forward to set the transition point.

Preferably, the surgical device includes a lock that may be engaged to lock the handle of the rod in place relative to the wand for holding the bag in a desired position without the surgeon having to hold the device. Bag positions may include degrees of openness ranging from completely closed to wide open, depending on the extent to which the rod is bowed.

Methods of using the surgical device comprise the steps of directing the device into the body cavity, opening the bag by pushing the rod handle forward, receiving the mass from the body cavity into the bag, and closing the bag by pulling the handle backwards.

The invented reclosable pouch device may be used with one hand and allows controlled and accurate movements inside the body cavity. Supporting and moving the bag with the wand and rod, having the axis of the bag entryway generally perpendicular to the longitudinal axis of the device, and having control over the degree of openness of the bag result in excellent maneuverability. The invented device may close the bag to provide an excellent seal for enclosing and retaining solids and liquids inside the bag. An option of adjusting the transition point of the rod allows for different sizes and shapes of bags and bag openings.

Other objects, advantages and novel features of the invention will become apparent to those skilled in the art from the following detailed description, wherein I have shown and described only the preferred embodiments of the invention, simply by way of illustration of the best mode contemplated by us of carrying out the invention. As will be realized, the invention is capable of other and different embodiments and use in other applications, and its several details are capable of modification in various obvious respects, all without departing from the invention. Accordingly, the drawings and descriptions are to be regarded as illustrative in nature, and not as restrictive.

BRIEF DESCRIPTION OF THE DRAWINGS

FIG. 3A is a top view of the embodiment of FIG. I, in an open position.

FIG. 3B is a top view of the embodiment of FIG. 1, in a partially open position.

FIG. 3C is a top view of the embodiment of FIG. 1, in a closed position.

FIG. 4 is a right side view of another embodiment of the invention, in a closed position and including an adjustable connector.

FIG. 5A is a cross-sectional view of the back end of the wand and the handle of the rod, as viewed along the line 5—5 in FIG. 4, illustrating the preferred channel system.

FIG. 5B is a cross-sectional view of the back end of the wand and the handle of the rod, as viewed along the line 5—5 in FIG. 4, illustrating the dovetail-shaped channel system.

FIG. 6 is a cross-sectional view of the front end of the wand and the flexible portion of the rod, as viewed along the line 6—6 in FIG. 4.

FIG. 7 is a top view of another embodiment of the invented device, with a bag attached and in the open position.

FIG. 8 is a cross-sectional view of the embodiment of FIG. 7, viewed along the line 8—8 in FIG. 7.

DETAILED DESCRIPTION OF THE INVENTION

Figure 1:
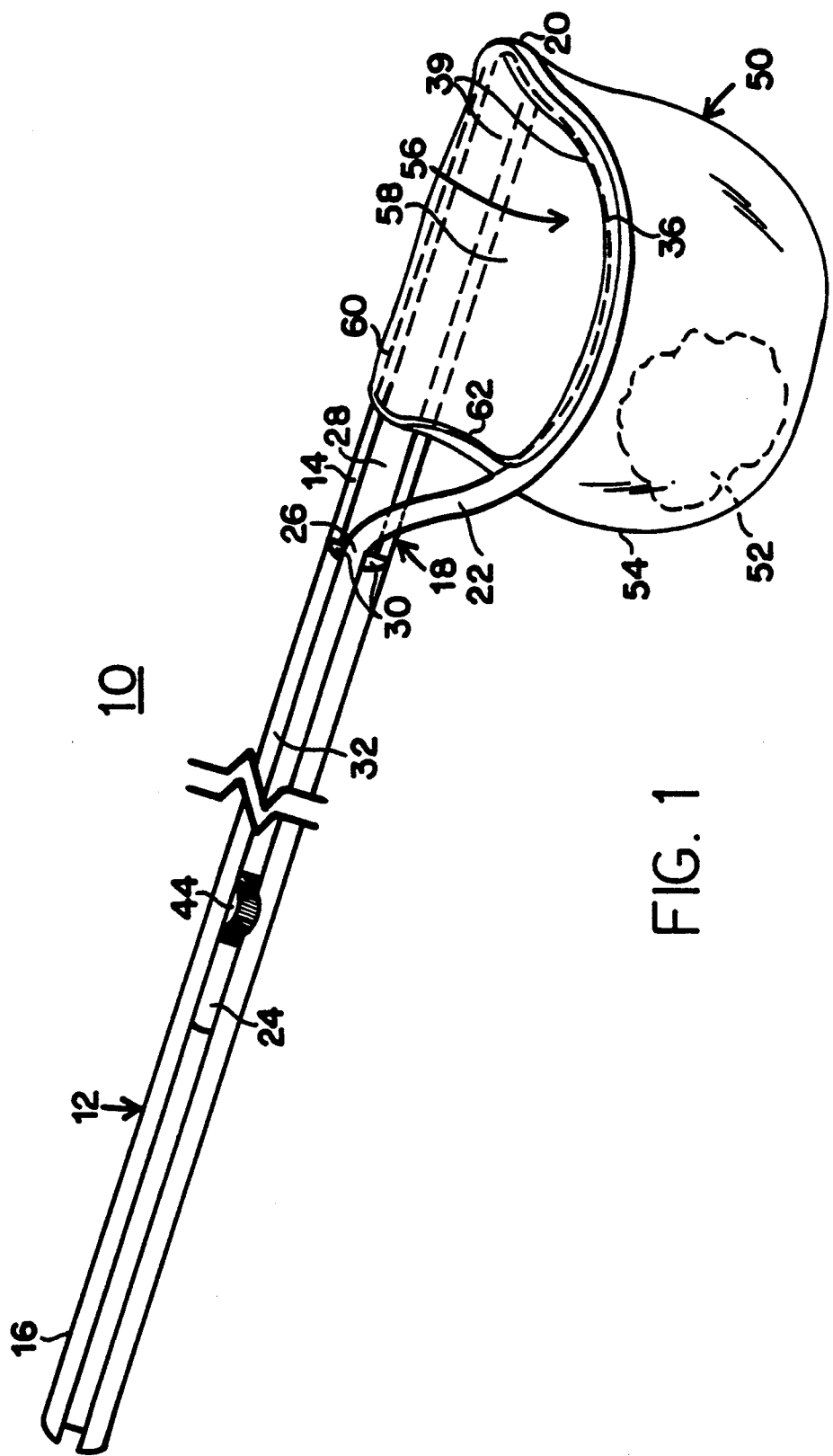
FIG. 1 is a perspective view of one embodiment of the invented device, including a bag in the open position and containing a mass.
Figure 2:
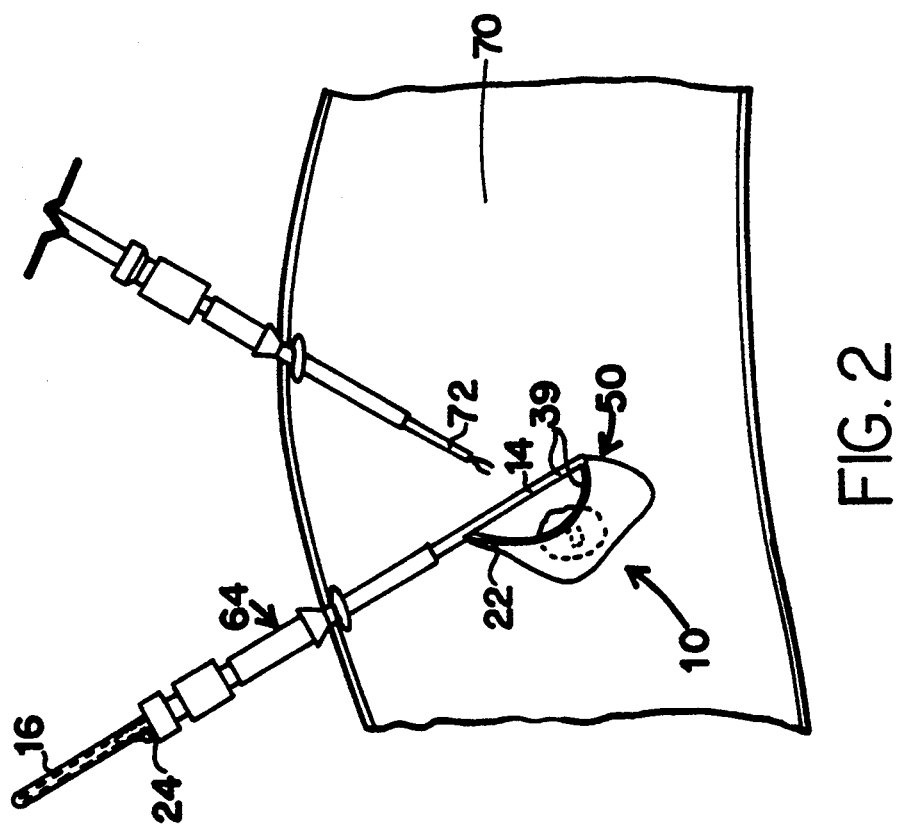
FIG. 2 is a view of the embodiment of FIG. 1 directed through a laparoscopic sleeve into a body cavity and opened for use in laparoscopic surgery.

Referring to FIGS. 1-8, there are shown some, but not the only, embodiments of the reclosable pouch surgical device 10. The reclosable pouch 10 has an elongated wand 12 with a front end 14 and a back end 16. An elongated rod 18 has a pivot end 20 that is attached to the front end 14, a flexible portion 22, and a handle 24 that extends back for lying generally parallel to the back end 16. The wand front end 14 and back end 16 serve as reference points for this discussion, so that "forward" and "front" refer to those movements or locations toward the front end 14 and "backward" and "back" refer to those toward the back end 16.

The pivot end 20 may be attached to the front end 14 preferably in a pivotal fashion, such as being hinged to let the flexible portion 22 bow out. Optionally, the pivot end 20 may be attached in a stationary fashion such as being welded. In embodiments using a stationary attachment, the flexibility of the flexible portion 22 allows it to bow out from the wand 12 near the pivot end 20 even though the pivot end 20 is not hinged.

In the preferred embodiment shown in FIG. 1, a slot system serves as a connector for holding the handle 2.4 close to the back end 16 and for extending forward to set the transition point 26, which is where the flexible portion 22 transitions from lying close to the wand 12 to bowing out from the wand 12. This transition point 26 may be anywhere on the flexible portion 22 between the handle 24 and the pivot end 20. However, designing a reclosable pouch 10 with the transition point 26 very close to the pivot end 20 would give little longitudinal distance in which the flexible portion 22 could bow. Therefore, the connector preferably extends forward to about the middle of the flexible portion 22.

The slot system includes a channel 28 and a lip 32. The channel 28 extends along the longitudinal axis of the wand 12 from the back end 16 and forward preferably to the location of the pivot end 20. The rod 18 is received in the channel 28. The lip 32 extends partially over the channel 28 for slidably holding the rod 18 in the channel 28 forward up to the location of the front extremity 30. At the front extremity 30 of the lip 32, the rod 18 may come out of the channel 28 to bow. An alternative embodiment could include a lip slanted to form a dovetail-shaped channel system as illustrated in FIG. 5B.

The channel 28 preferably extends all the way to the location where the pivot end 20 attaches to the front end 14, so that when the flexible portion 22 straightens, it may be received in the channel 28 to form a seal 34 between the front end 14 and the flexible portion 22, or, as explained below, between the first half 36 and second half 38 of the bag edge 39. Other designs may be used to allow the front end 14 and flexible portions 22 to cooperate to form a seal 34, such as the embodiment in FIGS. 7 and 8 in which the front and flexible portion inner surfaces 40',42' are flat.

To bow out the flexible portion 22, the surgeon pushes the handle 24 forward, preferably using the thumb grip 44 or some other means that aids comfortable operation. Because it is anchored at the pivot end 20, the rod 18 responds "to being pushed by bowing out. To straighten the flexible portion 22 and to bring it closer to the wand 12, the surgeon pulls the handle 24 backwards. Alternatively, the flexible portion 22 may be biased in the closed or unbowed position by allowing the flexible portion 22 to spring back to the unbowed position when pressure on the thumb grip 44 is released.

Preferably, the reclosable pouch 10 includes a means for detachably locking the handle 24 in a desired position, so that the surgeon may adjust the rod 18 with one hand, remove his or her hand, and have the rod 18 stay in that position until it is adjusted again. In the preferred embodiment, the handle is locked into position by means of a slight interference fit between the rod handle 24, channel 28, and lip 32, so that there is resistance to sliding unless the rod 18 is purposely moved by the surgeon. Alternatively, the handle can be locked into position by means of rough or raised surfaces on the channel 28 and handle 24 or a pin for snapping in against the rod 18 to bias it against a side wall of the channel 28.

The preferred embodiment includes a bag 50 for enclosing a mass 52, which may be opened and closed by the bowing and straightening action of the flexible portion 22. The bag 50 has a wall 54 for surrounding an interior space 56, an entryway 58 in communication with the interior space 56, and an edge 39 that surrounds the entryway 58. The bag 50 is preferably disposable and attached to the front end 14 and flexible portions 22 so that the bag 50 may be detached without any damage to the rest of the device. In the preferred embodiment, the edge 39 is attached to the front end 14 and flexible portions 22 by an adhesive, and the edge 39 extends between the inner surfaces 40,42 and is compressed when the bag 50 is closed. Approximately a first half 36 of the edge 39 is attached to the flexible portion 22 and the second half 38 is divided between a wand section 60 attached to the front end 14 and an unsupported section 62 extending between the front end 14 and flexible portions 22. The unsupported section 62 allows the flexible portion 22 to slide forward without tearing the edge 39 and to slide backward without pulling the edge 39 underneath the lip 32.

Another option for the bag attachment is to have the rod 18 be detachable from the wand 12 for slipping a sleeved-style bag edge onto the device. This option could include the connector being disconnectable, for example with the red 18 sliding all the way out of the slot system, or could include the pivot end 20 being detachable from the front end 14.

Regarding the flexibility of the wand 12, there are several options. The wand front end 14 may be rigid in some embodiments and somewhat flexible in other embodiments. For example, the front end 14 may be somewhat flexible for operations in which the surgeon needs to temporarily bend the wand to reach a particular location in the body cavity at a particular angle. However, the wand should be less flexible than the rod flexible portion 22, so that the flexible portion 22 bows out from the wand 12 when the handle 24 is pushed, rather than the flexible portion 22 and the wand front end 14 bending together in the same direction and thus producing either no opening of the bag 50 or a partial and difficult-to-control opening.

Regarding the flexibility of the rod 18, there are also several options. The flexible portion 22 should be of a flexibility in the outward direction that causes it to bow out relative to the wand 12 when it is pushed. The rod 18 may have a rigid handle 24 which may be held close to the wand 12 either by the hand of the person using it or by the laparoscopic sleeve 64. The rod 18 may also be flexible back to and including the handle 24, as long as a connector is included to hold and guide the handle 24 when it is being pushed and as long as the handle 24 flexibility is limited to a range which does not cause buckling and binding of the rod 8 inside the connector. In other words, the rod 18 may have a flexible portion 22 near the pivot end 20 and a relatively rigid handle 24', or may be a flexible rod with a flexible portion 22 and a flexible handle 24 which cooperates with a connector that holds and guides the handle 24.

Optionally, embodiments with a rigid handle 24' may also include a connector, such as the collar 66 shown in FIG. 7, for additional guiding of the handle 24'. FIG. 7 shows an example of the optional adjustable feature for a connector, the adjustable feature being for changing the longitudinal location of the connector front extremity 30' to change the rod transition point 26'. The collar 66 may be moved forward or backward to select a transition point 26' and then may be locked into place, for example with a set screw (not shown), in such a way that the rod 18' may still slide through the collar. An adjustable connector such as the collar 66 may also be added to embodiments having a slot system, as illustrated in FIG. 4. With the adjustable connector, the surgeon may use a single reclosable pouch with differently-sized bags or differently-shaped entryways, such as the wide entryway 58' in FIG. 7.

The preferred materials for the wand 12 and rod 18 are any materials that fulfill the various flexibility and rigidity requirements while also being safe for sterilization and internal surgery use. Surgical steel could be machined to meet these needs.

The preferred materials for the bag 50 should also meet sterility and safety requirements for internal surgery. Transparent plastics, flexible fabrics, and netting could be used. The preferred materials have some memory for tending to stay in a somewhat expanded state rather than tending to collapse, because this feature aids in the quick opening or unwrapping of the bag 50. The preferred materials are impermeable to liquid or are liquid-resistant, for containing infected liquids, but netting or loosely-woven materials could also be of benefit for some surgical procedures.

The method of using the reclosable pouch 10 includes directing the device with an attached bag 50 into a body cavity 70, preferably through a laparoscopic sleeve 64, so that back end 16 and handle 24 are accessible by the surgeon. The bag 50 is opened by pushing the handle 24 forward relative to the wand 12. The bag 50 is directed relative to the mass 52 so that the mass 52 moves through the entryway 58 into the interior space 56 of the bag 50. This may be done by moving the bag 50 to the mass 52 and scooping it up or by inserting the mass 52 into the bag 50 with another tool 72. The bag 50 may be closed for further manipulation of the mass 52 or for removal of the reclosable pouch 10 and mass 52 from the body cavity 70. To facilitate removal from the laparoscopic sleeve 64, the bag 50 may be wrapped around the front and flexible portions 14,22 to form a compact and smooth unit.

Optionally, a grinding, cutting, or other surgical tool 72 may be inserted into the interior space 56 of the bag 50 for further manipulation of the mass 52, for example, to cut a large mass into pieces that will fit through the laparoscopic sleeve. The tool 72 may be inserted before the bag 50 is closed, or after the bag 50 is closed if the flexible portion 22, front end 14, or bag 50 is adapted to allow a tool 72 to pass through the seal 34. Preferably, the flexible portion 22, front end 14, or bag 50 would also be adapted to maintain a good seal around the inserted tool 72 to prevent escape of mass and liquid.

Optionally, the tool 72 could be inserted into the body cavity 70 through the same laparoscopic sleeve 64 as the reclosable pouch 10, or through hollow passage in the wand 12.

While preferred embodiments of the invention have been shown and described, it will be apparent to those skilled in the art that various modifications may be made in these embodiments without departing from the spirit of the present invention.

I claim:

1. A surgical device for attachment to a bag for insertion of the bag through a laparoscopic sleeve into a body cavity and for manipulation of the bag to retrieve a mass, the surgical device comprising:

an elongated wand having a front end for placement in the body cavity and an opposing back end for extending out of the laparoscopic sleeve for access by the surgeon; and an elongated rod having a pivot end attached to the front end of the wand, a rigid handle opposing the pivot end and lying close and parallel to the back end of the wand for extending out of the laparoscopic sleeve for access by the surgeon, and a flexible portion between the pivot end and the handle of the rod, wherein the flexible portion bows out from the front end of the wand when the handle of the rod is pushed forward toward the front end of the wand and the flexible portion straightens to lie close and parallel to the front end of the wand when the handle of the rod is pulled backward away from the front end of the wand, and wherein the front end of the wand and flexible portion of the rod are adapted for securely receiving the bag so that when the flexible portion of the rod bows out, the bag opens, and when the flexible portion of the rod straightens, the bag closes, a connection means slidably connecting and holding close together the handle of the rod and the back end of the wand, and a sealing means wherein the flexible portion of the rod and the front end of the wand cooperate to seal the bag when the flexible portion straightens to lie close and parallel to the front end of the wand.

2. A surgical device as set forth in claim 1, wherein the connection means slidably engages the rod from the handle forward to the flexible portion, the connection means having a front extremity for determining a location where the flexible portion transitions from lying close and parallel to the wand to bowing out from the wand when the handle is pushed forward toward the front portion of the wand.

3. A surgical device as set forth in claim 2, wherein the connection means front extremity is adjustable in longitudinal location for adjusting the location at which the flexible portion of the rod transitions from lying close and parallel to the wand to bowing out from the wand.

4. A surgical device as set forth in claim 2, wherein the connection means comprises:

a channel in the wand for slidably receiving the rod, the channel extending longitudinally from the back end of the wand forward to where the pivot end of the rod is attached to the front end of the wand; and a lip extending from the back end of the wand near the channel for slidably holding the rod in the channel, the lip extending partially across the channel and the rod from the handle of the rod forward to the flexible portion of the rod so that the lip slidably holds the rod in the channel and close and parallel to the wand forward up to the front extremity.

5. A surgical device for attachment to a bag for insertion of the bag into a body cavity and for manipulation of the bag to retrieve a mass, the surgical device comprising:

an elongated wand having a front end for placement in the body cavity and an opposing back end for extending out of the body cavity for access by the surgeon;

an elongated flexible rod having a pivot end attached to the front end of the wand, a handle opposing the pivot end and lying close and parallel to the back end of the wand for extending out of the body cavity for access by the surgeon, and a flexible portion between the pivot end and the handle of the rod, wherein the flexible portion bows out from the front end of the wand when the handle is pushed forward toward the front end of the wand and the flexible portion straightens to lie close and parallel to the front end of the wand when the handle is pulled backward away from the front end of the wand; and a connection means slidably connecting and holding close together the handle of the rod and the back end of the wand, wherein the connection means engages the flexible rod from the handle forward to the flexible portion, the connection means having a front extremity for determining a location where the flexible portion transitions from lying close and parallel to the front end of the wand to bowing out from the front end of the wand, wherein the front end of the wand and flexible portion of the rod are adapted for securely receiving the bag so that, when the flexible portion bows out, the bag opens, and, when the flexible portion straightens, the bag closes.

6. A surgical device as set forth in claim 5, further comprising a lock means for detachably locking the handle in longitudinal position relative to the back end of the wand for holding the bag in a desired degree of openness.

7. A surgical device as set forth in claim 6, further comprising a sealing means, wherein the flexible portion of the rod and the front end of the wand cooperate to seal the bag when the flexible portion straightens to lie close and parallel to the front end of the wand.

8. A surgical device as set forth in claim 6, wherein the connection means front extremity is adjustable in longitudinal location for adjusting the said location at which the flexible portion of the rod transitions from lying close and parallel to the wand to bowing out from the wand.

9. A surgical device as set forth in claim 6, wherein the connection means comprises:

a channel in the wand for slidably receiving the rod, the channel extending longitudinally from the back end of the wand forward to where the pivot end of the rod is attached to the front end of the wand; and a lip extending from the back end of the wand near the channel for slidably holding the rod in the channel, the lip extending partially across the channel and the rod from the handle of the rod forward to the flexible portion of the rod so that the lip slidably holds the rod in the channel and close and parallel to the wand forward up to the front extremity.

10. A surgical device for insertion into a body cavity and for manipulation to retrieve a mass, the surgical device comprising:

an elongated wand having a front end for placement in the body cavity and an opposing back end for extending out of the body cavity for access by the surgeon, an elongated rod having a pivot end attached to the front end of the wand, a handle opposing the pivot end and lying close and parallel to the back end of the wand for extending out of the body cavity for access by the surgeon, and a flexible portion between the pivot end and the handle of the rod, wherein the flexible portion bows out from the front end of the wand when the handle is pushed forward toward the front end of the wand and the flexible portion straightens to lie close and parallel to the front end of the wand when the handle is pulled backward away from the front end of the wand;

a connection means slidably connecting and holding close together the handle of the rod and the back end of the wand, wherein the connection means engages the rod from the handle forward to the flexible portion, the connection means having a front extremity for determining a location where the flexible portion transitions from lying close and parallel to the front end of the wand to bowing out from the front end of the wand; and a bag having a wall defining an interior space, an entryway for communication with the interior space, and an edge surrounding the entryway and attached to the front end of the wand and the flexible portion of the rod, so that when the flexible portion bows, the bag opens and, when the flexible portion straightens, the bag closes.

11. A surgical method for manipulating and retrieving a mass from a body cavity, the method comprising:

directing a surgical device through a laparoscopic sleeve into the body cavity, the surgical device comprising:

an elongated wand having a front end and an opposing back end;

an elongated rod having a pivot end attached to the front end of the wand, a handle opposing the pivot end and lying close and parallel to the back end of the wand, and a flexible portion between the pivot end and the handle of the rod;

a connection means slidably connecting and holding close together the handle of the rod and the back end of the wand; and a bag having a wall defining an interior space, an entryway for communication with the interior space, and an edge surrounding the entryway and attached to the front end of the wand and flexible portion of the rod;

opening the entryway of the bag by pushing the handle of the rod forward toward the front end of the wand so that the flexible portion of the rod bows out from the front end of the wand;

directing the bag relative to the mass so that the mass moves through the entryway of the bag into the interior space of the bag; and closing the entryway of the bag by pulling the handle of the rod backward away from the front end of the wand so that the flexible portion of the rod straightens to lie close and parallel to the front end of the wand.

12. A surgical method as set forth in claim 11, wherein the surgical device further comprises a sealing means wherein the front end of the wand and flexible portion of the rod cooperate to seal the bag when the flexible portion straightens to lie close and parallel to the front end of the wand, and wherein the step of closing the entryway of the bag further comprises sealing the bag.

13. A surgical method as set forth in claim 11, further comprising the step of directing a surgical tool into the interior space of the bag after the mass has moved through the entryway of the bag into the interior space for access to the mass.

* * * * *